(12) United States Patent
Coventry

(10) Patent No.: US 8,007,753 B2
(45) Date of Patent: Aug. 30, 2011

(54) CATALYTIC OXIDATION OF HYDROCARBON GAS

(75) Inventor: Andrew Coventry, Queensland (AU)

(73) Assignee: Bantix Worldwide Pty Ltd., Queensland (AU)

( * ) Notice: Subject to any disclaimer, the term of this patent is extended or adjusted under 35 U.S.C. 154(b) by 614 days.

(21) Appl. No.: 11/911,636

(22) PCT Filed: Apr. 18, 2006

(86) PCT No.: PCT/AU2006/000521
§ 371 (c)(1),
(2), (4) Date: Sep. 12, 2008

(87) PCT Pub. No.: WO2006/108244
PCT Pub. Date: Oct. 19, 2006

(65) Prior Publication Data
US 2009/0209790 A1    Aug. 20, 2009

(30) Foreign Application Priority Data
Apr. 15, 2005    (AU) .................................. 2005901891

(51) Int. Cl.
*C01B 31/20* (2006.01)
*F01K 13/00* (2006.01)

(52) U.S. Cl. ........................................ 423/437.1; 60/645
(58) Field of Classification Search ............... 423/437.1; 60/645
See application file for complete search history.

(56) References Cited

U.S. PATENT DOCUMENTS
5,813,166 A      9/1998 Wigton et al.
6,817,140 B1    11/2004 Durand et al.
2003/0037550 A1*  2/2003 Fassbender ..................... 60/772

FOREIGN PATENT DOCUMENTS
WO    99/37145 A1    7/1999
WO    2004/082376 A1    9/2004

OTHER PUBLICATIONS
International Search Report for Application No. PCT/AU2006/000521, 2006.

* cited by examiner

*Primary Examiner* — Jafar Parsa
(74) *Attorney, Agent, or Firm* — Caesar, Rivise, Bernstein, Cohen & Pokotilow, Ltd.

(57) ABSTRACT

A process for the catalytic oxidation of a hydrocarbon gas comprising the steps of releasing pulses of a compressed hydrocarbon gas into an expansion chamber (8) and passing the expanded hydrocarbon gas over a catalytic converter (11) to oxidize the hydrocarbon gas.

12 Claims, 2 Drawing Sheets

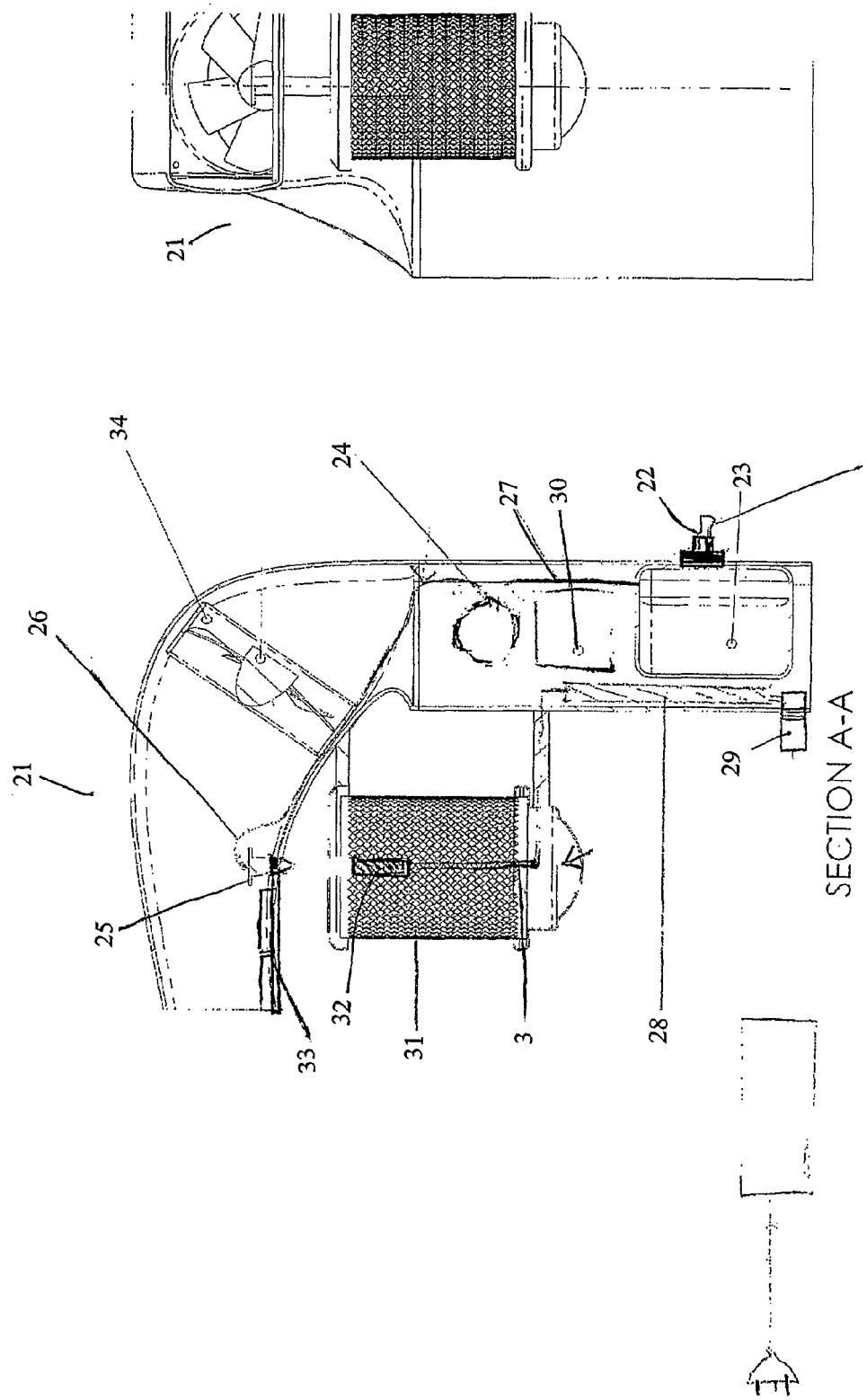

US 8,007,753 B2

CATALYTIC OXIDATION OF HYDROCARBON GAS

CROSS-REFERENCE TO RELATED APPLICATIONS

This national stage application claims the benefit under 35 U.S.C. §371 of International Application No. PCT/AU2006/000521 filed on Apr. 18, 2006, entitled CATALYTIC OXIDATION OF HYDROCARBON GAS, which in turn takes its priority from Australian Application No. 2005901891 filed on Apr. 15, 2005, and all of whose entire disclosures are incorporated by reference herein.

BACKGROUND OF THE INVENTION

1. Field of Invention

The present invention relates to a process for the oxidisation of a hydrocarbon gas. In particular, the present invention relates to a process for the oxidation of a hydrocarbon gas to generate carbon dioxide and heat.

2. Description of Related Art

Hydrocarbon gases, such as LPG (liquefied petroleum gas) have been used in many applications for the generation of heat. For example, LPG has been used as a fuel for cooking, hot water appliances, heating appliances, heating the boiler of an absorption fridge, as well as a myriad of other applications. The hydrocarbon gas is generally supplied from a pressurised cylinder such as a gas bottle or the like. In order for the compressed gas to be delivered to the appliance for use as a fuel, the pressurised gas is feed through a regulator to both reduce and control the pressure of the gas being fed to the appliance. The appliances use a continuous flow of fuel at a reduced and controlled pressure for combustion. A continuous burning flame is used for the combustion of the fuel and produces carbon dioxide.

Many insects, such as mosquitoes detect carbon dioxide and use the detected carbon dioxide to locate a warm blooded mammal. Generally mammals do not expel carbon dioxide in a continuous manner but in a periodic manner through the process of breathing. The generation of carbon dioxide to attract insects such as female mosquitoes is known. However, processes used for the generation for carbon dioxide for attracting such insects have been limited to the continuous generation of carbon dioxide. This is because of the need for the reliable combustion of the hydrocarbon gas and the technical complexities involved in the regular and frequent periodic combustion of a hydrocarbon gas. The need to periodically ignite and extinguish the hydrocarbon gas generally renders such a process uneconomic and technically unfeasible at any realistic cost.

Similarly, in many applications where a hydrocarbon gas is used as a fuel for combustion, it is necessary to either continuously combust the hydrocarbon gas or to operate a pilot light continuously in order that the fuel can be ignited on demand. Such uses generally result in an excess of hydrocarbon fuel being consumed or provide an increased safety risk due to the continuous presence of a flame.

BRIEF SUMMARY OF THE INVENTION

We have found a process for the oxidation of a hydrocarbon gas that overcomes at least one of the deficiencies identified above, or providing the consumer with a useful or commercial choice. According to the present invention, there is provided a process for the catalytic oxidation of a hydrocarbon gas comprising the steps of releasing pulses of a compressed hydrocarbon gas into an expansion chamber and passing the expanded hydrocarbon gas over a catalytic converter to oxidize the hydrocarbon gas.

In a second aspect, the present invention provides a catalytic oxidiser for hydrocarbon gas comprising a source of compressed hydrocarbon gas in communication with an expansion chamber wherein a valve for releasing pulses of compressed hydrocarbon gas is disposed therebetween, said oxidiser further comprising a catalytic converter in communication with the expansion chamber.

The hydrocarbon gas oxidised by the process of the present invention may be any of a variety of hydrocarbon gases as maybe available from time to time for combustion. Suitable hydrocarbon gases for use in the present invention include LPG (liquefied petroleum gas), LNG (liquid natural gas) as well as any of the alkanes.

LPG is generally a mixture of hydrocarbon gases that consist substantially of a mix of propane and butane but typically also contains propylene and butylene present in minor concentration. Other components of lesser concentration may also be present in LPG resulting from either the manufacturing process or added to facilitate the use of the LPG. For example, ethyl mercaptam is often added to LPG due to its strong odour whereby any leaks of LPG can readily be detected.

Propane is another preferred hydrocarbon gas for use in the present invention. Propane is conveniently available as a compressed gas for use as a fuel.

The hydrocarbon gas for use in the present invention is compressed. The use of a compressed gas is necessary for efficient storage and transport. Typically, the compressed gas is compressed to approximately the pressure at which it becomes liquid, resulting in even more efficient storage and transport. For example, liquid petroleum gas becomes a liquid at about 6 bar.

Preferably the compressed gas is provided as a bottled gas and is substantially in liquid form contained in the pressurised bottle. Typically the compressed hydrocarbon gas is at a pressure of about 150 psi, although the pressure will be dependant upon the outside temperature. The compressed hydrocarbon gas is released into an expansion chamber in a series of pulses. The compressed gas may be released through a valve of a gas bottle such that a predetermined amount of gas is released into the expansion chamber. The gas may be released from the bottle without the need for a regulator by releasing the compressed gas through a restrictor tube into a valve, such as an electronically controlled valve and then into another restrictor tube that is connected to the expansion chamber.

In a preferred embodiment, the gas may be released from the gas bottle through a porous ceramic slug. The use of a porous ceramic slug also alleviates the need for a regulator on the gas bottle. The porous ceramic slug is mounted in the gas take off line from the gas bottle. The porous ceramic is preferably of the type suitable for use in brake linings which permits water to pass through the porous ceramic but retains oil. The porous ceramic includes an interconnected network of interstices through which the passage of gas is restricted.

A control unit which may be operated by an electronic or mechanical timer may control the release of pulses of compressed gas. Generally, only a small amount of compressed gas is released such that the pressure of the gas as it exits the expansion chamber is at or below the desired level. It will be appreciated that as gas exits the expansion chamber the pressure of the gas decays until the next burst of compressed gas is released into the expansion chamber. In order to provide accurate control over the release of compressed gas a small diameter orifice. This small diameter orifice may be provided in an electronic valve which is attached directly to a bottle or via a restrictor hose. Typically, an orifice of approximately one $32^{nd}$ of an inch is desirable. In this way, small amounts of gas may be released in a controlled manner.

The valve from the source of compressed gas may pulse the hydrocarbon gas into a thin tube which controls the flow of the gas by pulsing the compressed hydrocarbon gas into the expansion chamber.

It is preferred that an electronic control unit is provided to pulse the release of compressed hydrocarbon gas. It is preferred that the electronic control unit be powered by either mains electricity or a battery that is maintained in a charged state by the generation of electrical power using the process of the present invention. The use of an electronic control unit enables a number of safety features to be incorporated into the process of the present invention. For example, if the temperature of the catalytic converter rises above a predetermined limit, the process may be terminated and an alarm triggered. This may be caused by the valve jamming open. If the temperature falls below a predetermined limit, the process may be terminated and an alarm triggered. Where the temperature falls below a predetermined limit, a lack of hydrocarbon gas may be the cause and it may be necessary to replace the source of hydrocarbon gas, or it may be that the element has failed and the gas has not ignited on start up Alternatively, the catalytic converter may have been destroyed and require replacement.

The electronic control unit may also control the operation of a heating element, described below, that may be used to pre-heat the catalytic converter to a desired temperature at which the catalytic oxidation of the hydrocarbon gas may be operated. The electronic control unit may be used to detect the temperature of the catalytic converter and heat, when necessary, the catalytic converter prior to the release of the compressed hydrocarbon gas.

The process of the present invention comprises the release of the compressed hydrocarbon gas into an expansion chamber. The expansion chamber can be of any convenient construction and sized to provide sufficient volume to reduce the pressure of the compressed hydrocarbon gas to a desired level. Typically, the pressure to which the compressed gas is reduced once it is released into the expansion chamber is approximately 100 psi but it will be appreciated that the pressure may vary with the temperature of the gas.

The expansion chamber may be of any convenient configuration In a preferred embodiment the expansion chamber may be a 3 inch length of 1½ inch diameter copper pipe. The expansion chamber may contain a desecant inside to absorb moisture from the gas. A thin wire filter may be used to prevent contaminants in the gas from blocking the outlet restrictor pipe. The expansion chamber may have a restrictor pipe extending from the valve at one end and another restrictor pipe extending to the converter at the other end. A pipe forming the expansion chamber may be squashed at each end and restrictor pipes may be welded into the ends so the gas comes in and expands (drops pressure) and then as it is still under pressure it is forced to go through the outlet restrictor pipe.

Once the compressed gas is released into the expansion chamber the pressure is reduced to the desired level and the expanded hydrocarbon gas is still at a pressure that forces the gas to be passed over the catalytic converter. As the expanded hydrocarbon gas passes from the expansion chamber, the pressure of the expanded gas decays over time until little or no hydrocarbon gas is being passed over the catalytic converter until the next burst a few seconds later.

The expanded hydrocarbon gas is passed to the catalytic converter through a narrow tube that is preferably five times the length of the tube between the compressed gas source and the expansion chamber. Without wishing to be bound by theory, it is believed that this gives the gas the correct amount of restriction through friction, etc. to reduce the pressure to the desired pressure. We have found that the longer the restrictor pipe, the greater the restriction thus the lowering of volume and pressure.

As the gas escapes from the expansion chamber through the narrow tube leading to the catalytic converter, preferably the expanded gas passes through a small jet outlet over the catalytic converter.

The catalytic converter may be of any convenient type used for the catalytic oxidation of a hydrocarbon gas. Suitably the catalytic converter may be formed from a ceramic substrate coated with a rhodenium or platinum catalyst. The catalytic converter may be of any convenient configuration such as a plate like construction. However, it is preferred that the catalytic converter be of a honeycomb construction so as to provide a high surface area.

The catalytic converter includes a heating element which is used to cause the ignition of the gas in one mode of operation, the heating element only stays on for a brief period, say three minutes, which heats the catalytic converter to a temperature which ensures the gas will catalytically oxidise. Once this catalytic oxidisation has started, it produces heat and causes the catalytic converter to be heated to a temperature at which the catalytic oxidation of the expanded hydrocarbon gas will continue to occur as long as a burst of gas is released before the catalytic converter cools, say within 5 seconds. The heating element may be an electric heating element powered by 12 volts either from a 12 power transformer from 110/240 volts or a 12 volt battery that may be maintained in a charged state by the operation of the process of the present invention. Typically an element requires approximately 3 amps to sufficiently heat the catalytic converter to cause the catalytic oxidation of the gas. A small lead acid battery can provide this amount of current for a short period, say three minutes to cause the effect. The heating element may also be controlled by an electronic controller that activates the heating element when the unit is required to start as set by an electronic control timer or a manual on/off switch.

In use, it is preferred that the frequency of the released pulses of compressed hydrocarbon gas that are catalytically oxidised is sufficient to maintain the catalytic converter at or above the desired temperature so that the process of the present invention may be operable without requiring any additional heating of the catalytic converter such as by using a heating element.

The catalytic conversion of the hydrocarbon gas generates carbon dioxide and water as the main components of the oxidisation. Other components will be produced by the oxidisation including carbon monoxide and other oxidation products of the alkanes and other components of the hydrocarbon gases. Advantageously, the pulsed release of hydro carbon gas over the catalytic converter provides a similarly pulsed release of carbon dioxide. The pulsed release of carbon dioxide advantageously mimics the release of carbon dioxide by a mammal such as a human and advantageously provides an attractant to a variety of insects such as female mosquitoes. This permits the process of the present invention to be used as an attractant for insects such as mosquitoes to draw them towards a suitable extermination device. In order to facilitate the release of carbon dioxide, the catalytic converter is open to the atmosphere.

The connection of the controller to the source of compressed hydrocarbon gas and the connection between the controller and the expansion chamber is preferably using a small capillary tube having an internal diameter of 0.026 of an inch. Advantageously, we have found by using a capillary tube of this type, it is possible to accurately meter the amount of compressed gas released by each pulse of the controller. Accordingly, we have found that this system does not require the use a regulator on the bottle so as to limit the volume and pressure. In an example of the use of the present invention, the gas is pulsed by the electronic control unit by activating the valve in short 1 second or half second bursts every 4 seconds (this can vary up to every 10 second intervals). This allows the gas, in small amounts, to enter into the chamber expand and then pass back out of the chamber at a slightly reduced pressure which is enough to allow the combustion on the hot catalytic converter. By controlling the pulsing of the gas release, greater efficiencies may be obtained. At elevated pressures the gas may not fully combust or not ignite and reduced pressures the gas may not be efficiency driven over the catalytic converter and may not fully combust or not ignite. By controlling the pulsing, both in the amount of gas released and the frequency, the pressure of gas may be maintained in a range that permits efficient combustion.

Using a capillary tube is also advantageous as a capillary tube is more likely to be self healing, that is in the event of a breakage of the capillary tube, it is more likely that the tube closes off because it is squashed or deformed by any such breakage. Furthermore, the covering of such a capillary tube with a heavy flexible rubber sheath permits the making of a hose that is both cheap and relatively safe. In addition, the use of a heavy rubber sheaf reduces the likelihood of kinking of the capillary tube. Most importantly the capillary tube preferably has an internal diameter in the range of from 0.66 mm or 0.026 of an inch and is made from soft drawn copper giving it the ability to hold huge pressure of gas because of the small diameter and thick wall size. This restrictor pipe is of the type that is commonly used in domestic and commercial refrigeration and air conditioning.

The capillary tubes used on the inlet side of the expansion chamber and the outlet side of the expansion chamber are preferably of the same or similar internal diameter and about 0.026 of an inch in diameter. It is preferred that the capillary tube on the outlet side of the expansion chamber is at least five times the length of the capillary tube used on the inlet side of the expansion chamber as this gives the correct flow and restriction of the gas.

The process of the present invention may be put into effect in a number of applications. The process may be used to produce carbon dioxide to attract female mosquitoes into a mosquito trap. The process of the present invention produces bursts of carbon dioxide that may be timed so as to be similar to the expulsion of carbon dioxide by humans and animals that cause mosquitoes and other insects to be attracted.

The heat generated by the process of the present invention may be used to produce electrical power by a thermo electric power generation unit associated with the catalytic converter. The power generated is constant DC as the heat is passed onto a plate that maintains the heat as does the ceramic honeycomb. The operation temperature of thermo plates is from 50 degrees up to 200 depending on the type used and the thermocouples are placed on the plate hot on one side and cooled by a fan on the other side. The fan may be powered by the battery. Power that may be produced from the heat of the catalytic converter may be stored in a suitable battery, such as of the lead acid type, and this power be used to operate any desired electrical appliance including an electronic controller for the process of the present invention and/or a heating element for the pre-heating of the catalytic converter.

Particularly advantageously, the process of the present invention may be used to power an absorption refrigeration unit. The heat produced at the catalytic converter may be used to operate the boiler of an absorption refrigeration unit without the need for a continuous flame. Also, the electrical energy that may be produced and stored in an appropriate battery, may be used to provide a fan to provide air movement inside the refrigeration unit as well as a fan to move external heat away from the condenser of the refrigeration unit. In this way, the absorption refrigeration unit may be made more efficient without requiring a power source other than the hydrocarbon gas fuel.

Advantageously, the process of the present invention provides safe and economical conversion of hydrocarbon gas into heat, carbon dioxide and water without the use of a flame for the combustion of the hydrocarbon gas. No spark or flame is required in order to initiate the oxidation process as the oxidation process is a catalytic oxidation that is initiated by the passage of the expanded hydrocarbon gas over a catalytic converter.

Furthermore, the process of the present invention permits the oxidation of a hydrocarbon gas without the need for the use of a regulator to reduce the pressure of stored compressed gas to a pressure suitable for use. The pulsed nature of the operation of the present invention allows the reduction in pressure to be achieved using a simple expansion chamber.

BRIEF DESCRIPTION OF SEVERAL VIEWS OF THE DRAWINGS

The present invention will now be described with reference to the accompanying non-limiting drawings, provided to illustrate the present invention.

FIG. 2 is a catalytic oxidiser for mounting on an absorption style refrigerator.

DETAILED DESCRIPTION OF THE INVENTION

Figure 1:
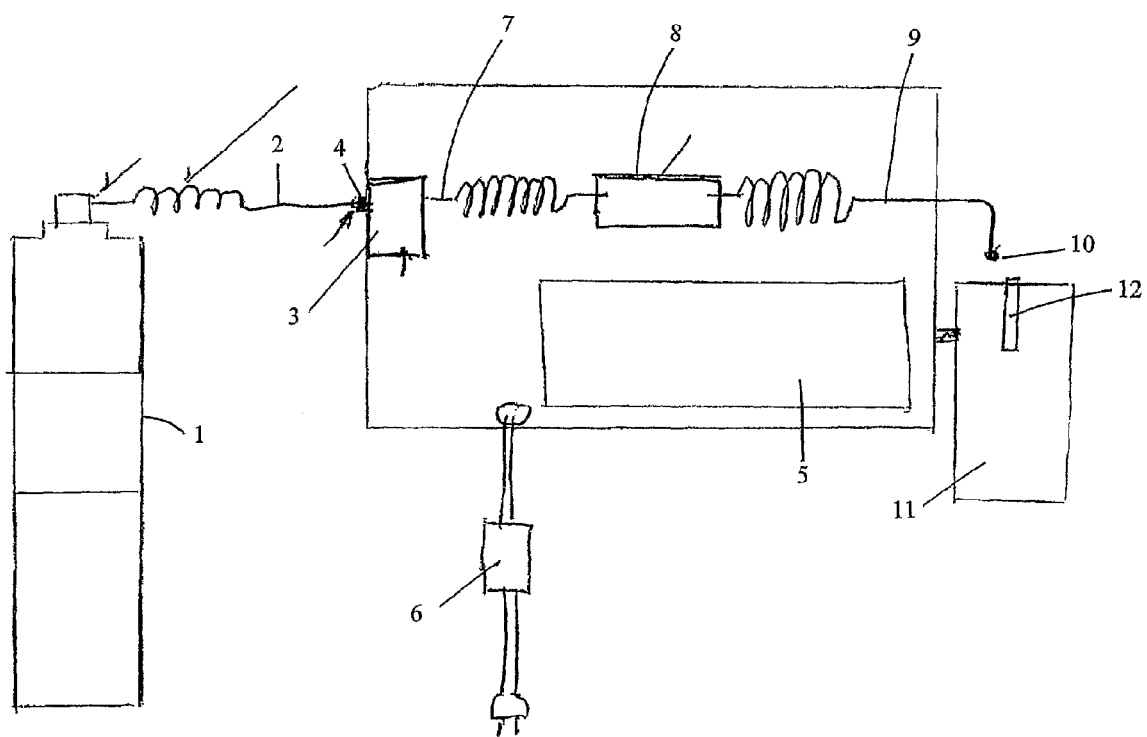
FIG. 1 is a schematic diagram of an apparatus for the conduct of the process of the present invention.

FIG. 1 shows a bottle of compressed propane 1. The bottle 1 is connected to a copper gas hose 2 which is a 0.026 capillary copper tube covered with a rubber sleeve (not shown). The gas hose 2 is directly connected to the gas bottle 1 with no regulator therebetween. The gas hose 2 is connected to an electronic valve 3 by a suitable fitting 4.

The electronic valve 3 is operated on a 12 volt circuit and actuated by a control circuit board 5. The control circuit board 5 is connected to a suitable power source which may be a transformer 6 that is connectable to a 110/240 volt supply.

The electronic valve 3 is connected to a capillary tube 7 that is also formed from copper pipe and has an internal diameter of 0.026 inch. The capillary tube 7 is connected to a gas expansion chamber 8 that is formed from a three inch length of 1½ inch diameter copper pipe.

A capillary outlet tube 9 is connected to the gas expansion chamber 8 and directs the expanded propane through a nozzle 10 into a ceramic honeycomb support coated with a suitable catalyst such as platinum or rhodenium. The honeycomb support has a heating element 12 disposed within the catalytic converter.

In operation compressed propane gas is fed via the electronic valve 3 into the gas expansion chamber 8. The electronic valve 3 releases pulses of compressed gas into the gas expansion chamber 8. As these pulses of compressed gas expand within the expansion chamber 8 they are released through the nozzle 10 over the catalytic converter 11. The heating element 12 enables the catalytic converter to be brought up to and maintained at a suitable temperature for the catalytic oxidation of the propane. The control circuit board 5 controls the electronic valve 3 as well as the heating element 12. A temperature sensor such as a thermo-couple may be provided on the catalytic converter 11 to provide feedback to the control board 5 so as to effectively operate the heating element 12.

FIG. 2 shows an absorption type refrigerator 21 which may be connected to a suitable source of compressed gas by hose connector 22. Electronic valve 23 releases pulses of compressed gas to expansion chamber 24. Expansion chamber 24 is connected to a gas jet 25 through a capillary tube 26. Similarly, the electronic valve 23 is connected to the expansion chamber 24 by a capillary tube 27. A control board 28 is connected to a suitable power supply via a plug 29. The plug 29 maybe connected to a 12 volt transformer that may connect to the mains power. A 12 volt battery 30 is provided to provide backup power where mains power is unavailable.

A ceramic honeycomb catalytic converter 31 is disposed on the refrigerator 21 in close proximity to the boiler (not shown) of the refrigeration unit so as to operate the absorption system. The catalytic converter 31 includes an element 32 for heating the catalytic converter. The heating element is connected to the control board 28.

A thermo-electric plate is provided adjacent the catalytic converter to re-charge the battery 30 and to maintain it in an operational state. Where the refrigeration unit is not connected to a mains power supply the electrical power generated by the thermo-electric plate 33 is sufficient to operate by the catalytic oxidiser as well as the fan 34 which is used to blow cool air over 1 side of the thermo-electric plate.

Pressure Testing For CO2 Generator

Equipment used:—
Gasmate 9 kg LPGas cylinder.
Gasmate LPG Regulator.
Comweld Pressure Gauges.
Capillary hose for LPG, SP6 tubing (0.055 in bore×24 in long)
High pressure hose for oxygen tests.
Test 1:—
True pressure in LPG cylinder.
With 2 kg of gas 150 psi
With full cylinder 150 psi
Test 2:—
True pressure through Gasmate regulator approximately 1 to 2 psi.
Test 3:—
Flow through regulator and capillary tubes. (flow was so small, the tubes were immersed in water so flow could be examined). Test was conducted through SP6 tubing (0.055 in bore) and through SP1 tubing (0.026 bore). Flow without regulator sufficient for operation of system.
This test shows that we do not require a standard gas regulator to reduce the pressure in the 0.026 capillary tube as the resistance of the capillary tube is sufficient for the gas to provide the pressure needed to allow the gas to be forced through the capillary and onto the converter.
Test 4:—
This is without the pressure reducing expansion chamber
A test was done using the SP6 capillary and a SP1 nozzle with fall bottle pressure (150 psi), but the flow was too strong to be used in the CO2 generator.

Test 5:—
High pressure testing was undertaken using a bottle of compressed oxygen and a high pressure hose.
The units tested were pressure reducing coils.

|  |  | Inlet pressure | Outlet Pressure |
|---|---|---|---|
| Pressure | SP6 Coil: - | 150 psi | 150 psi |
|  |  | 300 psi | 300 psi |
|  |  | 450 psi | 450 psi |
|  | SP1 Coil: - | 150 psi | 100 psi |
|  |  | 300 psi | 270 psi |
|  |  | 450 psi | 430 psi |

Conclusions:—

The results of the LPG testing clearly indicated that a standard pressure reducer need not be used as there was insufficient flow to allow combustion at the face of the catalytic converter.

Full bottle pressure proved to be too strong for efficient operation over the catalytic converter, and flow through the larger capillaries was also too strong. The unit that proved most successful was the SP1 coil running directly from the LPG bottle through the valve and then the expansion chamber with valve bursts of between half a second up to 2 seconds long with at least a 2 second gap between bursts. This combination reduced the pressure just enough to allow correct combustion and allows only approximately half to 1 gram of gas to be expelled onto the hot ceramic allowing full change of the propane to co2. Any longer bursts or more gas and the unit did not efficiently convert propane gas and a residual amount would be expelled into the atmosphere as well as $CO_2$.

Those skilled in the art will appreciate that the present invention may be subject to variations and modifications other than those specifically described. It is to be understood that the present invention encompasses all such variations and modifications that fall within its spirit and scope.

What is claimed is:

1. A process for the catalytic oxidation of a hydrocarbon gas which comprises the steps of:
    (i) passing a hydrocarbon compressed gas from a source of said compressed gas through a first capillary tube connected to said compressed gas source wherein said first capillary tube is of relatively small diameter;
    (ii) causing said compressed gas after passage through said first capillary tube to flow through an electronic valve to cause said compressed gas to flow in intermittent pulses;
    (iii) passing said flow of compressed gas into an expansion chamber of substantially greater size than said first capillary tube to expand said compressed gas and also to reduce the pressure of the compressed gas;
    (iv) causing said expanded and pulsed gas after step (iii) to flow through a second capillary tube of relatively small diameter which is substantially longer in length than the first capillary tube to reduce both volume and pressure of the expanded and pulsed gas under the influence of friction, and;
    (v) after passing through said second capillary tube passing said expanded gas through a catalytic converter for catalytic oxidation of the expanded gas to form carbon dioxide.

2. A process according to claim 1 wherein the hydrocarbon gas is selected from the group consisting of liquified petroleum gas, liquid natural gas and compressed propane.

3. A process according to claim 1 wherein the pressure to which the compressed gas is reduced once it is released into the expansion chamber is approximately 100 psi.

4. A process according to claim 1 wherein the temperature of the catalytic converter is monitored and maintained by controlling the flow of compressed hydrocarbon gas over the catalytic converter as well as by the application of heat by heating elements.

5. A process according to claim 1 wherein the catalytic converter is formed from a ceramic substrate coated with a rhodenium or platinum catalyst.

6. A process according to claim 1 wherein the catalytic converter is of a honeycomb construction so as to provide a high surface area.

7. A process according to claim 1 wherein the first and second capillary tubes have an internal diameter of about 0.026 of an inch.

8. A process according to claim 1 wherein heat generated by the process is used to produce electrical power by a thermo electric power generation unit associated with the catalytic converter.

9. A process accounting to claim 1 wherein in the electronic valve is controlled by a control unit or circuit board operated by an electrical board operated by an electrical or mechanical timer to control release of pulses of said compressed gas.

10. A process according to claim 1 wherein there is no regulator in the connection of the first capillary tube to the source of compressed gas.

11. A process according to claim 1 wherein the length of the second capillary tube is five times the length of the first capillary tube.

12. A process according to claim 1 wherein said carbon dioxide after release from said catalytic converter is used to attract insects.

* * * * *